United States Patent
Katano et al.

(10) Patent No.: US 8,945,886 B2
(45) Date of Patent: Feb. 3, 2015

(54) METHODS FOR PRODUCING POLYUNSATURATED FATTY ACID AND LIPID CONTAINING POLYUNSATURATED FATTY ACID

(75) Inventors: Kenji Katano, Osaka (JP); Hiroshi Kawashima, Osaka (JP)

(73) Assignee: Suntory Holdings Limited, Osaka-shi, Osaka (JP)

(*) Notice: Subject to any disclaimer, the term of this patent is extended or adjusted under 35 U.S.C. 154(b) by 348 days.

(21) Appl. No.: 12/523,087

(22) PCT Filed: Jan. 15, 2008

(86) PCT No.: PCT/JP2008/050313
§ 371 (c)(1),
(2), (4) Date: Mar. 3, 2010

(87) PCT Pub. No.: WO2008/087921
PCT Pub. Date: Jul. 24, 2008

(65) Prior Publication Data
US 2010/0167359 A1    Jul. 1, 2010

(30) Foreign Application Priority Data
Jan. 15, 2007    (JP) .................................. 2007-006293

(51) Int. Cl.
*C12P 7/64*    (2006.01)
*C12N 1/14*    (2006.01)
(Continued)

(52) U.S. Cl.
CPC .............. *C12P 7/6472* (2013.01); *A23K 1/1846* (2013.01); *C11B 3/00* (2013.01); *A23K 1/164* (2013.01); *A23L 1/3008* (2013.01); *A23K 1/188* (2013.01); *C12P 7/6427* (2013.01); *C11B 1/10* (2013.01)

USPC ......................................... 435/134; 435/254.1

(58) Field of Classification Search
None
See application file for complete search history.

(56) References Cited

U.S. PATENT DOCUMENTS

| 5,658,767 A * | 8/1997 | Kyle .............................. 435/134 |
| 2002/0156254 A1* | 10/2002 | Qiu et al. ..................... 536/23.1 |
| 2006/0174376 A1* | 8/2006 | Renz et al. .................... 800/281 |

FOREIGN PATENT DOCUMENTS

| EP | 1359224 | * | 5/2003 |
| JP | 02-086789 | | 3/1990 |

(Continued)

OTHER PUBLICATIONS

Hiroshi Kawashima et al., "Industrial Production of Dihomo-γ-Linolenic Acid by a Δ5 Desaturase—Defective Mutant of *Mortierella alpina* 1 S-4 Fungus", Journal of the American Oil Chemists' Society, 2000, pp. 1135-1138, vol. 77, No. 11.*

(Continued)

*Primary Examiner* — Blaine Lankford
*Assistant Examiner* — Lauren K Van Buren
(74) *Attorney, Agent, or Firm* — Drinker Biddle & Reath LLP

(57) ABSTRACT

A method for producing a polyunsaturated fatty acid (PUFA) or a lipid containing a PUFA, a microbial cell containing a PUFA, and use of the microbial cell are provided. A method for producing a polyunsaturated fatty acid (PUFA) or a lipid containing a PUFA including culture of a microorganism capable of producing arachidonic acid (ARA) and/or dihomo-gamma-linolenic acid (DGLA) is provided, the method including at least one of the following steps: (a) adding an organic acid in an amount of 0.01 to 5 w/v % to a culture medium after the beginning of main culture; (b) increasing the pH of the culture medium to a range effective for culture after the beginning of the main culture; and (c) adding a metal sulfate in an amount of 0.01 to 0.5 w/w % to the main culture medium.

6 Claims, 2 Drawing Sheets

(51) Int. Cl.
    C12N 1/20    (2006.01)
    A23L 1/30    (2006.01)
    A23K 1/18    (2006.01)
    C11B 3/00    (2006.01)
    A23K 1/16    (2006.01)
    C11B 1/10    (2006.01)

(56) References Cited

FOREIGN PATENT DOCUMENTS

JP          5091887 A     4/1993
JP       2006055071 A     3/2006

OTHER PUBLICATIONS

Hiroshi Kawashima et al., "Industrial Production of Dihomo-γ-Linolenic Acid by a Δ5 Desaturase—Defective Mutant of *Mortierella alpina* 1S-4 Fungus", Journal of the American Oil Chemists' Society, 2000, pp. 1135-1138, vol. 77, No. 11.

Shimizu et al., "Production of useful fatty acids by microbial processes," Recent Res. Devel. in Lipids Res., 1 (1997), pp. 267-286.

Supplemental European Search Report issued May 3, 2013, by the European Patent Office in EP 08 70 3177.

Nagao Totani et al., "The Role of Morphology During Growth of *Mortierella alpina* in Arachidonic Acid Production", Journal of Oleo Science, 2002, pp. 531-538, vol. 51, No. 8.

Hiroshi Kawashima et al., "Industrial Production of Dihomo-γ-Linolenic Acid by a Δ5 Desaturase-Defective Mutant of *Mortierella alpina* 1S-4 Fungus", Journal of the American Oil Chemists' Society, 2000, pp. 1135-1138, vol. 77, No. 11.

Hiroshi Kawashima, "Arachidonic Acid and Dihomo-γ-Linolenic Acid—Microbial Production and Physiological Function", Foods & Food Ingredients Journal of Japan, 2005, pp. 106-114, vol. 210, No. 2 (English Abstract).

Byung-Hae Hwang et al., "High-Level Production of Arachidonic Acid by Fed-Batch Culture of *Mortierella alpina* Using $NH_4OH$ as a Nitrogen Source and pH Control," Biotechnology Letters, 2005, pp. 731-735, vol. 27.

Shigeaki Fujikawa et al., "Production of Arachidonic Acid-Containing Triacylglycerol by Filamentous Fungi," Bioscience & Industry, 1999, pp. 818-821, vol. 57, No. 12 (Japanese).

International Search Report mailed Mar. 11, 2008 in International Application No. PCT/JP2008/050313 filed Jan. 15, 2008.

* cited by examiner

METHODS FOR PRODUCING POLYUNSATURATED FATTY ACID AND LIPID CONTAINING POLYUNSATURATED FATTY ACID

CROSS REFERENCE TO RELATED APPLICATIONS

This application is the National Stage of International Application No. PCT/JP2008/050313, filed Jan. 15, 2008, and claims benefit of Japanese Application No. 2007-006293, filed Jan. 15, 2007, both of which are herein incorporated by reference in their entirety.

TECHNICAL FIELD

The present invention relates to methods for producing a polyunsaturated fatty acid (PUFA) and a lipid containing a PUFA, a microbial cell containing a PUFA, and use of the microbial cell. In particular, the present invention relates to methods for producing a lipid with a high content of dihomo-gamma-linolenic acid (DGLA) or arachidonic acid (ARA) and a microbial cell containing the lipid, and representative use of the microbial cell.

BACKGROUND ART

Polyunsaturated fatty acids (hereinafter referred to as PUFAs) have a variety of useful physiological functions. PUFAs herein refer to fatty acids containing 20 or more carbon atoms and having two or more double bonds. In recent years, PUFAs, in particular, dihomo-gamma-linolenic acid (hereinafter referred to as DGLA) and arachidonic acid (hereinafter referred to as ARA) have been found useful in varied ways (Non-Patent Literature 1). For example, it has been found that DGLA has an inhibitory effect on atopic dermatitis and an antiallergic effect and ARA has a brain function improvement effect and a nutrient effect for infants. In addition, there is concern about lack of DGLA and ARA in patients afflicted with adult diseases including potential patients, infants, elderly people, and pets (in particular, animals of the feline family).

Under such circumstances, various investigations on supply of PUFAs, in particular DGLA or ARA, have been carried out. Culturing microorganisms capable of producing such fatty acids has been studied as practical processes. Various investigations on such processes have also been carried out to find a process suitable for industrial production (Non-Patent Literature 1). For PUFAs (in particular, DGLA), a large-scale method of culture was found that yielded up to 167 g of DGLA for 1 kg of dry microbial cell (Patent Literature 1 and Non-Patent Literature 2). In these methods, however, division of the culture medium and addition of glucose must be frequently repeated for at least several days from the beginning of the culture in order to avoid low productivity due to consumption of a large amount of glucose during the beginning of the culture and growth inhibition that results from high glucose concentration.

Furthermore, methods of culture for microorganisms have been studied to improve the productivity of particular substances. Patent Literature 2 discloses a method for culturing *Kluyveromyces lactis* in a culture medium containing whey to produce cerebroside by fermentation, which includes addition of various sodium sources to the culture medium, and control of the pH of the culture medium.

In addition, with culture of the genus *Mortierella* (filamentous fungus) Non-Patent Literature 3 discloses a method for controlling the pH using $NH_4OH$, which is also used as a nitrogen source, whereas Patent Literature 3 discloses control of the pH within the range of 7 to 7.5 in the latter half of the culture period. Non-Patent Literature 4 discloses addition of 0.05% $CaCl_2 \cdot 2H_2O$, 0.05% $MgCl_2 \cdot 6H_2O$, and 0.1% $Na_2SO_4$ together with $KH_2PO_4$ to a culture medium leads to fungus in an optimal form and an increase in the productivity of PUFA.

[Patent Literature 1] Japanese Patent No. 3354581
[Patent Literature 2] JP-A-2006-55070
[Patent Literature 3] U.S. Pat. No. 5,658,767
[Non-Patent Literature 1] Hiroshi Kawashima, Foods Food Ingredients J Jpn, 210, 106-114 (2005)
[Non-Patent Literature 2] H Kawashima et al., J Am Oil Chem Soc, 77, 1135-1138 (2000)
[Non-Patent Literature 3] Byung-Hae Hwang et al., Biotechnol Lett, 27, 731-5 (2005)
[Non-Patent Literature 4] Shigeaki Fujikawa et al., Bioscience and Industry, 57, 818-821 (1999)

DISCLOSURE OF THE INVENTION

Problems to be Solved by the Invention

As mentioned above, various investigations on methods for producing PUFAs, in particular DGLA and ARA by culturing microorganisms capable of producing fatty acids have been carried out. Microbial cells obtained by these conventional methods, however, have a disadvantage in that the content of PUFAs in the microbial cells is low. Microbial cells containing PUFAs can be added to foods and drinks, nutrition compositions, folders, or pet foods without further process after drying. At a low content of PUFA in microbial cells, however, a large number of microbial cells must be added in order to achieve a sufficient effect of PUFA, resulting in significantly limited contents of other components added. In addition, microbial cells containing PUFAs can be used as a low material to extract a lipid containing PUFAs. At low contents of PUFAs in microbial cells, however, a large number of microbial cells must be processed, which requires a large-scale extracting device and a large amount of extracting solvent. This will cause increased costs and increased energy consumption for the processing that cause significant environmental burden.

In the above conventional methods, various methods for controlling the culture of microbial cells have also been attempted. Since a complicated culture process leads to contamination, risk of handling errors, and increased costs, it is important to perform culture efficiently through minimized procedures including addition of additives to a culture medium.

The present invention was accomplished in view of the above-mentioned situation. An object of the present invention is to provide a low-cost method that is easy to handle and suitable for large-scale production of a PUFA or a lipid containing a PUFA, a microbial cell that contains a high content of PUFA or lipid containing the PUFA, and use of the microbial cell.

Means for Solving the Problems

Until now, addition of fat and oil and salts to a basal culture medium has been investigated as a culture technique to increase productivity of PUFA from filamentous fungi of the genus *Mortierella*, but addition of organic acids to find an increase in the PUFA content has never been attempted although the attempt using organic acids in other microorganisms has been made. In addition, optimal control of pH during culture has not been reported in detail. Moreover, no one has drawn attention to the effects of a combination of addition of organic acids and control of pH on the production of PUFA, although it is known that addition of organic acids naturally causes a reduction in pH.

In addition, with the content of metal salts added in trace amounts in a culture medium, for example, Non-Patent Literature 4 using $CaCl_2$ and $MgCl_2$ mainly focuses on only effects of $Ca^{2+}$ and $Mg^{2+}$, but not effects of the anions pairing with the metal ions. Accordingly, no one has focused on effects of the anions pairing with the metal ions on the productivity of PUFA from microorganisms.

In an addition procedure of additives to a basal culture medium, the culture medium is usually thermally sterilized before culture. Sterilization, however, is not usually carried out after mixing of glucose and other compounds due to high possibility of induction of a chemical reaction. Thus, addition of additives other than glucose to a culture medium at the beginning of the culture significantly complicates the culture process. Accordingly, the addition procedure must be simplified as much as possible with the proviso that simultaneous sterilization of glucose and other compounds, which are easy to cause chemical reaction, is avoided.

The inventors have intensively studied to solve the above problems and discovered that, in a method for producing a PUFA or a lipid containing a PUFA which involves aeration spinner culture of *Mortierella alpina* in a liquid culture medium, the contents of the lipid produced in a microbial cell, and of PUFAs, in particular DGLA and ARA, in the lipid can be dramatically increased by one of the following steps: (a) adding an organic acid and/or a salt thereof to a culture medium for culture; (b) increasing the pH of the culture medium to a certain range at a given time after the beginning of the culture; (c) adding a metal sulfate to the culture medium; and any combination thereof. In addition, the inventors further investigated the timing of steps (a) to (c), discovered that steps (a), addition of organic acid, and (b), control of pa of the culture medium, can be carried out at the same time, and accomplished the present invention.

The present invention provides a method for producing a polyunsaturated fatty acid (PUFA), preferably arachidonic acid (ARA) and/or dihomo-gamma-linolenic acid (DGLA), preferably DGLA, or a lipid containing the PUFA, preferably triglyceride, including culture, preferably aeration spinner culture of a microorganism capable of producing ARA and/or DGLA, preferably a microorganism belonging to the genus *Mortierella*, more preferably *Mortierella alpina* in a liquid culture medium, the method including at least one of the following steps (a) to (c):

(a) adding an organic acid, preferably at least one organic acid selected from organic acids contained in glycolysis pathway and its branched pathways or a TCA cycle, more preferably at least one organic acid selected from succinic acid, fumaric acid, pyruvic acid, lactic acid, and mane acid, most preferably succinic acid to a culture medium in an amount of 0.01 to 5 w/v %, desirably 0.2 to 5 w/v %, preferably 0.22 to 5 w/v %, more preferably 0.3 to 5 w/v %, most preferably 0.44 to 5 w/v % after the beginning of the main culture, desirably during a fatty acid accumulation stage, preferably in 24 hours or later, more preferably in three days or later, most preferably four days or later, after the beginning of the main culture;

(b) increasing the pH of the culture medium to a range effective for culture, desirably to the range of 6 to 8, preferably 6.3 to 7.5, more preferably 6.6 to 7.5, most preferably 6.9 to 7.2 after the beginning of the main culture, desirably during the fatty acid accumulation stage, preferably in 24 hours or later, more preferably in three days or later, most preferably in four days or later, after the beginning of the main culture; and (c) adding a metal sulfate, preferably at least one metal sulfate selected from $MgSO_4$, $CaSO_4$, $Na_2SO_4$, $K_2SO_4$, $FeSO_4$, and $MnSO_4$, more preferably $MgSO_4$ and/or $CaSO_4$, in an amount of 0.01 to 0.5 w/w %, preferably 0.01 to 0.25 w/w %, more preferably 0.05 to 0.2 w/w %, most preferably 0.06 to 0.1 w/w % to the main culture medium, these sulfates being suitably added instead of the corresponding metal chlorides in the culture medium.

The present invention also provides the method including steps (a) and (b), wherein steps (a) and (b) are carried out preferably on the same clay, more preferably at the same time, and at different times, preferably on different days from the addition of a carbon source such as glucose to the culture medium.

The present invention also provides the method including step (c), wherein step (c) is carried out before the beginning of the main culture.

The present invention also provides the method, wherein the DGLA content in the total fatty acids is 35 w/w % or more, preferably 37 w/w % or more, more preferably 40 w/w % or more in the PUFA or the lipid containing the PUFA.

The present invention also provides a dry cell of *Mortierella alpina*, wherein the DGLA content in one gram of dry cell is 190 mg or more, preferably 195 mg or more, more preferably 200 mg or more, most preferably 220 mg or more.

The present invention also provides a dry cell of *Mortierella alpina* prepared by drying a microbial cell of *Mortierella alpina* that is prepared by a method of culture in a liquid culture medium, the method including at least one of the following steps:

(a) adding at least one organic acid selected from succinic acid, fumaric acid, pyruvic acid, lactic acid, and malic acid, preferably succinic acid to the culture medium in an amount of 0.2 to 5 w/v %, preferably 0.22 to 5 w/v %, more preferably 0.3 to 5 w/v %, most preferably 0.44 to 5 w/v % in three days or later, preferably in four days or later, after the beginning of the main culture;

(b) increasing the pH of the culture medium to the range of 6.6 to 7.5, preferably 6.9 to 7.2, in three days or later, preferably in four days or later, after the beginning of the main culture; and (c) adding at least one metal sulfate selected from, for example, $MgSO_4$, $CaSO_4$, $Na_2SO_4$, $K_2SO_4$, $FeSO_4$, and $MnSO_4$, preferably $MgSO_4$ and/or $CaSO_4$ in an amount of 0.05 to 0.2 w/w %, preferably 0.06 to 0.1 w/w % to the main culture medium, these sulfates being suitably added instead of the corresponding metal chlorides in the culture medium.

The present invention also provides foods and drinks, preferably dietary supplements, drinks, fodders for animals, more preferably fodders for animals (in particular, pet foods) containing the above-mentioned dry cell or ARA and/or DGLA derived from the dry cell.

Furthermore, the present invention provides a PUFA obtained by the method mentioned above, preferably ARA and/or DGLA, or a lipid containing one of these, more preferably triglyceride.

Furthermore, the present invention provides the method, wherein the content of the resultant DGLA in one gram of dry microbial cell is increased by at least 3%, preferably at least 5%, more preferably at least 10%, compared with a method not including steps (a) to (c).

Furthermore, the present invention provides the method, wherein the content of the resultant ARA in one gram of dry microbial cell is increased compared with a method not including steps (a) to (c).

Furthermore, the present invention provides the method, wherein the DGLA content in mL of the culture medium after the end of the culture is at least 5.5 mg, preferably at least 6.5 mg, more preferably at least 7.0 mg, most preferably at least 7.5 mg.

Furthermore, the present invention provides the method, wherein the DGLA content in 1 mL of the culture medium after the end of the culture is increased by at least 5%, preferably at least 10%, more preferably at least 15%, compared with a method not including steps (a) to (c).

Furthermore, the present invention provides the method, wherein the ARA content in 1 mL of the culture medium after the end of the culture is increased, compared with a method not including steps (a) to (c).

Advantages of the Invention

According to a method of the present invention, the content of a PUFA in a microbial cell or a lipid containing a PUFA is dramatically increased. Accordingly, a microbial cell containing a PUFA, a PUFA, and a lipid containing a PUFA can be effectively utilized. In addition, in the present invention, since step (c) (addition of metal sulfates) can be carried out prior to the main culture, and step (a) (addition of the organic acid) and step (b) (control of the pH of the culture medium) can be carried out after the time required for the addition of glucose at the beginning of the main culture, a complicated process for addition of glucose on the same day for these processes can be avoided. As a result, the present invention can provide a low-cost method that is easy to handle, and suitable for large-scale production of a PUFA or a lipid containing a PUFA, a microbial cell with a high content of PUFA or lipid containing a PUFA, and use of the microbial cell.

BEST MODE FOR CARRYING OUT THE INVENTION

Microorganisms

Figure 1A:
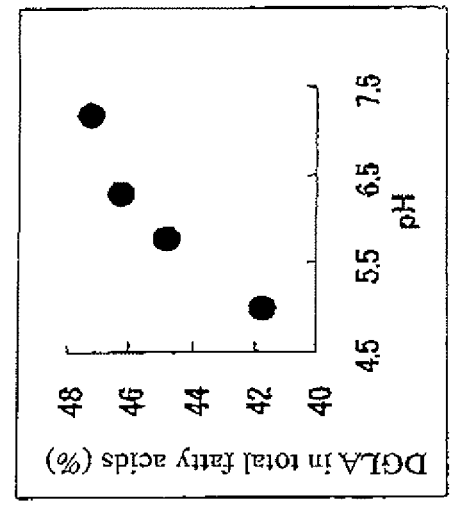
FIGS. 1A to 1C are graphs showing the effects on the DGLA content in cases where the pH was controlled (at pH 5.0, 5.8, 7.2) in five days after the beginning of the main culture of *Mortierella alpina* S14 in Example 4.

Examples of microorganisms that can be used in a method of the present invention include microorganisms capable of producing ARA and/or DGLA. Among these preferred are filamentous fungi of the genus *Mortierella*, more preferred are filamentous fungi of the subgenus *Mortierella*, and most preferred are *Mortierella alpina*. Examples of microorganisms capable of producing a lipid (triglyceride) containing arachidonic acid as a constituent fatty acid include microorganisms belonging to the genus *Mortierella*, genus *Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium*, and genus *Saprolegnia*.

Examples of microorganisms belonging to the subgenus *Mortierella* of the genus *Mortierella* include *Mortierella clongata*, *Mortierella exigua*, *Mortierella hygrophila*, and *Mortierella alpina*. Specific examples of strains of such microorganisms include *Mortierella* elongata IFO8570, *Mortierella* exigua IFO8571, *Mortierella* hygrophila IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, and CBS754.68.

These all strains can be available freely from, for example, Institute for Fermentation, Osaka (IFO), American Type Culture Collection (ATCC) in the United States, and Centraal Bureau voor Schimmelcultures (CBS). In addition, strains isolated from soil by the study group of the present invention, for example, *Mortierella alpina* 1S-4, *Mortierella clongata* SAMO219 (FERM P-8703) (FERM BP-1239), as well as *Mortierella alpina* 814 and *Mortierella alpina* Iz3 derived from 1S-4 by an ordinary mutation operation, nitrosoguanidine treatment, can also be used.

In addition, examples of microorganisms that can be used in a method of the present invention include mutants of the microorganisms mentioned above. For example, a microorganism belonging to the subgenus *Mortierella* can be subjected to a imitation process to construct mutant strains in which the activity of desaturase or elongase is reduced, lost, or improved. The mutation can be carried out by any technique known in persons skilled in the art. It can be easily understood by persons skilled in the art whether the mutant strains have desired productivity of PUFA or not.

Basic Culture Operation

The present invention provides methods for producing a polyunsaturated fatty acid (PUFA) and a lipid containing a PUFA, the methods including culture of the microorganisms mentioned above.

A method for inoculating a cell to a culture medium during culture of the microorganisms mentioned above can be properly selected by persons skilled in the art according to the culture process. Specifically, nurse cells, spores and/or hyphae of the microorganism strains, a seed culture solution prepared by preculture, or nurse cells, spores and/or hyphae collected from the seed culture solution are inoculated to a liquid or solid culture medium for culture.

Examples of carbon sources in the culture medium used in a method of the present invention include glucose, fructose, xylose, saccharose, maltose, amylogen, molasses, glycerol, mannitol, sucrose, sorbitol, galactose, and saccharified starch. Such carbon sources can be used alone or in combination. Furthermore, raw materials containing these carbon sources and commonly used by these skilled in the art, for example, citrus molasses, beet molasses, beet juice, or sugarcane juice can also be used without restriction.

Examples of usable nitrogen sources include nitrogen sources generally used by persons skilled in the art, such as natural nitrogen sources, e.g., peptone, yeast extract, malt extract, meat extract, casamino acid, corn steep liquor, soy protein, defatted soybean, and cottonseed meal; organic nitrogen sources, e.g., urea; and inorganic nitrogen sources, e.g., nitrates such as sodium nitrate and ammonium nitrate, and ammonium salts such as ammonium sulfate, ammonium chloride, and ammonium phosphate. In particular, nitrogen sources derived from soybeans, specifically soybeans, defatted soybeans, soya flakes, edible soy protein, bean curd refuse, soybean milk, and toasted soybean powder can be used. For example, heat-denatured defatted soybeans, more preferably defatted soybeans heated at about 70 to 90° C. free of ethanol-soluble component can be used alone or in combination thereof, or in combination with the above nitrogen sources.

In addition, phosphate ion, potassium ion, sodium ion, magnesium ion, calcium ion, metal ions of, for example, iron, copper, zinc, manganese, nickel, or cobalt, and vitamins can optionally be used as a micronutrient source. Optionally, antifoaming agent such as Adecanate can also be added.

The concentrations of such components in a culture medium are not particularly limited within a range that does not inhibit growth of microorganisms. Practically, the total amount of carbon sources to be added in a culture medium is desirably 0.1 to 40 w/w %, preferably 1 to 25 w/w %, and the total amount of nitrogen sources to be added is 2 to 15 w/w %, preferably 2 to 10 w/w %. In addition, it is known that the growth of microorganisms may be inhibited when the initial concentration of nitrogen sources and/or carbon sources is too high during the main culture. In a preferred embodiment, the initial amount of carbon sources to be added is 1 to 8 w/w %, preferably 1 to 5 w/w %, and the initial amount of nitrogen sources to be added is 0.1 to 8 w/w %, preferably 1 to 6 w/w %, and the carbon and nitrogen sources are added in amounts that have been consumed by microorganisms during the culture. It is known that sterilization after mixing of glucose and other compounds has high possibility of induction of a chemical reaction, and a high carbon/nitrogen ratio leads to high productivity of lipids from microorganisms. Thus, in a particularly preferred embodiment, culture is carried out by, for example, continuous supply of only carbon sources to a culture medium.

In addition, in order to increase the content of a lipid containing a PUFA in a microbial cell, for example, hydrocarbons such as hexadecane and octadecane; fatty acids such as oleic acid and linoleic acid or salts thereof, and fatty acid esters (for example, ethyl esters, glycerin fatty acid esters, and sorbitan fatty acid esters); and fats and oils such as olive oil, soybean oil, canola oil, cotton seed oil, and coconut oil can be added to a culture medium alone or in combination as precursors of unsaturated fatty acids. The amounts of such precursors to be added in a culture medium are in the range of 0.001 to 10 w/w %, preferably 0.05 to 10 w/w %. In addition, these precursors may be cultured as the only carbon source in a culture medium.

Culture may be any conventional culture of microorganisms, specifically, static culture, shaking culture, or aeration spinner culture. Examples of usable culture processes include so-called batch fermentation, fed-batch fermentation, repeated-batch fermentation, and continuous fermentation. Examples of usable agitation means include an impeller (agitating blade), air-lift fermenter, pump-driven circulation of fermentation broth, and combination thereof.

The method of the present invention can be performed by the methods of culture mentioned above. In particular, it is industrially advantageous to carry out a main culture by aeration spinner culture in a liquid culture medium. For example, stirred vessels such as a jar fermentor and a tank can be used for aeration spinner culture, but the vessels are not limited thereto.

For the aeration spinner culture, for example, oxygen-containing gas such as air or non-oxygen-containing gas such as argon and nitrogen may be fed. Such gas can be properly selected by persons skilled in the art under conditions for the culture system. For example, in the procedures described in Examples below (the case of *Mortierella alpina* in one embodiment of the present invention), oxygen-containing gas such as air is bubbled through the culture medium.

The culture temperature for microorganisms depends on the type of the microorganisms to be used, but generally 5 to 40° C., preferably 20 to 30° C. In one embodiment, microorganisms can be cultured at 20 to 30° C. to grow the cells, and further cultured at 5 to 20° C. to produce a lipid containing a PUFA. Such temperature control can also lead to an increase in the PUFA content in a lipid containing a PUFA.

When the microorganisms are cultured in a test tube or a flask (preculture stage), the culture period is generally one to ten days, preferably one to five days, more preferably one to three days. The culture period of the subsequent main culture is generally two to thirty days, preferably five to twenty days, more preferably five to fifteen days. The desired content of PUFA and the fatty acid composition can be criteria to determine the end of the main culture. The main culture can be divided into the following main periods: a logarithmic growth stage of microorganisms, that is, a period that involves an increase in the lipid free cell content (the dry cell weight of microorganisms minus the total fatty acid weight in the cell), and a subsequent accumulation stage of fatty acids such as PUFA, that is, a period that involves a small change in the lipid free cell content. Non-Patent Literature 4 discloses that the culture of *Mortierella alpina* 1S-4 in a 10 kL culture tank has a growth stage from the beginning of the culture to the second day (the lipid free cell content increases) and a subsequent fatty acid accumulation stage (the lipid free cell content does not substantially vary). The logarithmic growth stage and the fatty acid accumulation stage can be determined according to the description in Non-Patent Literature 4.

It should be noted that the pH of the culture medium is adjusted to the range of 5 to 7, preferably 5.5 to 6.5 at the beginning of the main culture of microorganisms (at addition of the seed culture medium).

Organic Acids

The present invention provides methods for producing a PUFA and a lipid containing a PUFA, including culture of microorganisms, each method including (a) adding an organic acid in an amount of 0.01 to 5 w/v % to a culture medium after the beginning of main culture. The addition of an organic acid to the culture medium can be carried out according to, for example, Examples described below.

The organic acids used in step (a) include organic acids and salts and hydrates thereof. Hereinafter, these may be collectively referred to as "organic acids". The organic acids in this specification refer to organic compounds having —COOH groups that do not inhibit growth of microorganisms when added in an amount of 0.01 to 5 w/v % to the culture medium. Among them preferred are, in particular, those contained in the glycolysis pathway and its branched pathways or a TCA cycle. Glycolysis and a TCA cycle are primary pathways for production of energy from the starting substance glucose, and for synthesis of fatty acid. Most of these pathways are involved by organic acids. Such organic acids are interconverted via glycolysis, a TCA cycle, and also its branched pathways or bypass pathways. Generally, fatty acid synthesis, which is the first stage of PUFA synthesis, requires acetyl CoA or NADPH produced in these pathways, and are closely involved in the pathways. Accordingly, the PUFA productivity of microorganisms will vary depending on the content and the balance of organic acids in a culture medium. In particular, when microorganisms are cultured in a culture medium containing organic acids, the preferred organic acids can increase the PUFA content per unit weight of a dry microbial cell, and/or the PUFA content per unit volume of the culture medium. Examples of such usable organic acids include at least one of succinic acid, fumaric acid, pyruvic acid, lactic acid, and malic acid (these are mono- or di-carboxylic acids each that contains three to four carbon atoms and may have one —OH group) and salts and hydrates thereof. Preferably used are at least one of succinic acid, malic acid, and lactic acid and salts and hydrates thereof. The usable salts of organic acids are at least one of sodium salt, potassium salt, magnesium salt, calcium salt, and ammonia salt. Whether the organic acids are preferable for addition or not can be determined by, for example, the technique described in Examples below.

These organic acids can be added in an amount of 0.01 to 5 w/v %, desirably 0.2 w/v % or more, preferably 0.22 w/v % or more, more preferably 0.3 w/v % or more, most preferably 0.44 w/v % or more (in term of the free organic acid content) in the culture medium. A content of 0.01 w/v % oar less may preclude achievement of an increase in the content of a PUFA or a lipid containing a PUFA in the microorganisms mentioned above. A content of 5 w/v % or more may lead to growth inhibition of the microorganism. In addition, it is believed that the content of a PUFA or a lipid containing a PUFA in the microorganisms does not necessarily increase in response to an increase in the amount of the organic acids to be added exceeding a certain level. Thus, the amount of the organic acids to be added can properly be selected within the range exceeding a certain level. In one preferred embodiment, 1 w/v % disodium succinate hexahydrate, which corresponds to 0.44 w/v % succinic acid, can be added to the culture medium. The organic acids, for example, in the form of solution can be added to the culture medium. Such organic acid solutions may be added after adjustment of the pH to a value similar to that of the culture medium. Alternatively, the pH of the organic acid solutions can be adjusted to a different value from that of the culture medium to change the pH of the culture medium.

These organic acids are added during the main culture of microorganisms, preferably after (not before) the beginning of the main culture. Since the effect of the addition of the organic acids is believed to occur during the fatty acid accumulation stage, the organic acids are added to a culture medium after the beginning of the main culture of microorganisms, suitably at the beginning of the fatty acid accumulation stage after the end of the logarithmic growth stage, for example, in 24 hours or later, preferably in three days or later, more preferably in four days or later, after the beginning of the main culture. In particular, the organic acids can be added in three to five days after the beginning of the main culture, for example in four days after the beginning of the main culture. In addition, the organic acids can be added at a time or several times. For case of the process, addition at a time is preferred.

pH

The present invention provides methods for producing a PUFA and a lipid containing a PUFA including culture of the microorganisms mentioned above, each method including (b) increasing the pH of the culture medium to a range effective for culture after the beginning of the main culture. The pH of the culture medium can be controlled, for example, according to Examples described below. The pH of the culture medium during the culture is believed to affect microorganism metabolism and, in particular, highly affect fatty acid synthesis or desaturation involved by the electron transport chain.

The pH of the culture medium can be controlled by techniques known in persons skilled in the art, such that the pH is higher than the pH of the culture medium before the control and is within a range which does not preclude growth of microorganisms (within a range effective for culture). For example, the pH of the culture medium can be increased to the range of 6 to 8, in view of the pH of the culture medium before the control. This range is preferably 6.3 to 7.5, more preferably 6.6 to 7.5, most preferably 6.9 to 7.2.

The pH can preferably be controlled with an alkaline solution of, for example, NaOH, KOH, NaHCO$_3$, or ammonia. In particular, a NaOH solution can be preferably used that is easily available at a low price and may have little adverse effect on the microorganisms mentioned above.

It is known that the pH of the culture medium adjusted to 0.5 to 7, preferably 5.5 to 6.5 at the beginning of the main culture of the microorganism mentioned above generally decreases once during the logarithmic growth stage of the microorganisms, then gradually returns to the original level, and slightly varies during the fatty acid accumulation stage. The pH of the culture medium is controlled during the main culture of the microorganisms mentioned above, preferably not before (that is, after) the beginning of the main culture. The effect of the pH control is believed to occur during the fatty acid accumulation stage. Thus, the pH is controlled after the beginning of the main culture of the microorganisms mentioned above, suitably at the beginning of the fatty acid accumulation stage after the end of the logarithmic growth stage, for example, in 24 hours or later, preferably in three days or later, more preferably in four days or later. In particular, it can be carried out most preferably in three to five days after the beginning of the main culture, for example, in four days after the beginning of the main culture. In addition, the pH may be continuously controlled for the period from the beginning of the pH control to the end of the culture, but preferably can be controlled at a time during the fatty acid accumulation stage due to the small change in the pH and for ease of the process.

Sulfate Salts

The present invention provides methods for producing a PUFA and a lipid containing a PUFA including culture of the microorganisms mentioned above, each method including (c) adding a metal sulfate to the main culture medium in an amount of 0.01 to 0.5 w/w %. The metal sulfate to the culture medium can be added according to, for example, Examples described below.

Examples of the metal sulfates include MgSO$_4$, CaSO$_4$, Na$_2$SO$_4$, K$_2$SO$_4$, FeSO$_4$, and MnSO$_4$. Among them preferred are MgSO$_4$ and CaSO$_4$. Such sulfates can be added alone or in combination. More preferably, sulfates such as MgSO$_4$ and CaSO$_4$ are added instead of the corresponding metal chlorides such as MgCl$_2$ and CaCl$_2$ in the culture medium. Hydrates thereof can also be used. The total amount of the hydrates that can be added is in the range of 0.01 to 0.5 w/w %, preferably 0.01 to 0.25 w/w %, more preferably 0.05 to 0.2 w/w %, most preferably 0.06 to 0.1 w/w % (excluding the weight of water molecules) in the culture medium.

MgSO$_4$ and/or CaSO$_4$ can be added together with Na$_2$SO$_4$ at the same time. In that case, the content of Na$_2$SO$_4$ is preferably at most 0.1 w/w % in the culture medium, and more preferably no Na$_2$SO$_4$ is added. In addition, MgSO$_4$ and CaSO$_4$ as metal sulfates can be added, for example, in an amount of 0.05 w/w % MgSO$_4$.7H$_2$O+0.05 w/w % CaSO$_4$.2H$_2$O, or 0.06 w/w % MgSO$_4$.7H$_2$O+0.06 w/w % CaSO$_4$.2H$_2$O in the culture medium.

The metal sulfate can be added to the culture medium either before or during the main culture. Unlike organic acids, the metal sulfate is preferably added at a time before the beginning of the main culture due to a low possibility of reaction with carbon sources such as glucose during sterilization and for ease of the process.

Steps (a) to (c) can be carried out individually or in combination. For example, steps (a) and (b) should be carried out in combination preferably on the same day, more preferably at the same time due to a potential variation in pH during step (a) and for ease of the process. For further ease of the process, these steps should not be carried out at the time when carbon sources such as glucose is added, and preferably should be carried out on different days from that for the addition of the carbon sources.

Furthermore, for example, the combinations of steps (a) and (c), steps (b) and (c), and steps (a), (b), and (c) are possible. In these cases, preferably step (c) is carried out before the beginning of the main culture, and steps (a) and/or (b) is carried out after the beginning of the main culture and on a different day from that for the addition of the carbon sources for ease of the process.

For one object of the present invention to provide a microbial cell with high content of PUFA, or lipid containing a PUFA, the combination of all steps (a), (b), and (c) is particularly preferred.

The culture procedure mentioned above can lead to production and accumulation of a lipid containing a PUFA in the cells of microorganisms.

Examples of the lipids contained in a microbial cell used in a method of the present invention include triglyceride, diglyceride, monoglyceride, phospholipid, lysophospholipid, glycophospholipid, and free fatty acids. In particular, the microbial cells mentioned above produce triglyceride as the main lipid.

The fatty acids constituting the lipid include PUFAs. The PUFAs are not particularly limited within the PUFAs that can be contained, produced, and accumulated in the microbial cells mentioned above. Examples of PUFAs include eicosadienoic acid, eicosatrienoic acid, dihomo-gamma-linolenic acid (DGLA), mead acid, eicosatetraenoic acid, arachidonic acid (ARA), eicosapentaenoic acid, docosadienoic acid, docosatrienoic acid, docosatetraenoic acid, docosapentaenoic acid, docosahexaenoic acid, tetracosadienoic acid, tetracosatriene acid, tetracosatetraenoic acid, tetracosapentaenoic acid, and tetracosahexaenoic acid. In a method of the present invention, microorganisms capable of producing, in particular, ARA and DGLA are used. Accordingly, particularly preferred PUFAs are ARA and DGLA, and DGLA is the most preferred. Also preferred PUFAs are DGLA, mead acid, ARA, and eicosapentaenoic acid, which can be produced through an improvement in a culture process for a microorganism belonging to the genus *Mortierella*, one of the microorganisms of the present invention (see Non-Patent Literature 1).

From the view point of one object of the present invention to provide a microbial cell with high content of PUFA or a lipid containing a PUFA, it is preferred that the content of PUFAs constituting a lipid be high in a microbial cell. When the PUFA is DGLA, the content of DGLA or the DGLA residue after the end of the culture of the microorganisms without addition of DGLA to the culture medium is more than 164 mg, for example, 190 mg or more, preferably 195 mg or more, more preferably 200 mg or more, most preferably 220 mg or more (in terms of the free fatty acid) in 1 g of dry cells as measured by the technique described in, for example, Examples below. In one embodiment, the content of the resultant DGLA in 1 g of dry cells can be increased according to a method of the present invention by, for example, 3% or more, preferably 5% or more, more preferably 10% or more (in terms of the free fatty acid) compared with a conventional method (not including steps (a) to (c)). In addition, in one embodiment, the content of the resultant ARA in 1 g of dry cells can be increased according to a method of the present invention compared with a conventional method (not including steps (a) to (c)).

Similarly, productivity per unit volume of the culture medium of a PUFA constituting a lipid contained in the microbial cells is desirably high. When the PUFA is DGLA, the yield of the DGLA or DGLA residue for 1 mL of the culture medium after the end of the culture of the microorganisms without addition of DGLA to the culture medium is 5.5 mg or more, preferably 6.5 mg or more, more preferably 7.0 mg or more, most preferably 7.5 mg or more (in terms of the free fatty acid), as measured by the technique described in, for example, Examples below. In one embodiment, the content of the resultant DGLA in 1 mL of the culture medium after the end of the culture can be increased in a method of the present invention by, for example, 5% or more, preferably 10% or more, more preferably 15% or more (in terms of the free fatty acid) compared with a conventional method (not including steps (a) to (c)). In addition, in one embodiment, the content of the resultant ARA in 1 mL of the culture medium after the end of the culture can be increased in a method of the present invention compared with a conventional method (not including steps (a) to (c)).

In one embodiment, the DGLA content in the total fatty acid is preferably high in a PUFA or a lipid containing a PUFA obtained by the method of the present invention, and is, for example, 35 w/w % or more, preferably 37 w/w % or more, most preferably 40 w/w % or more (in terms of the free fatty acid) as measured by the technique described in, for example, Examples below.

After the end of the culture, a PUFA, a lipid containing a PUFA, and microbial cells containing one of these can be recovered from the culture medium by any technique known in persons skilled in the art, for example, by the technique described in JP-A-2000-69987 or Examples below. The resultant PUFA or a lipid containing a PUFA is described above.

The cell is optionally sterilized, and then preferably dried. The drying step to obtain the dry microbial cell can be, for example, oven heating, lyophilization, and hot-air drying. For the microbial cells obtained from the culture medium after the end of the culture, the dry cells weight per unit volume of the culture medium is desirably high, and, for example, the dry cells weight for 1 ml of the culture medium is preferably about 34 mg or higher.

A lipid containing a PUFA can be recovered from a dry cell or a wet cell using any technique known in persons skilled in the art. For example, a dry cell is extracted with an organic solvent such as hexane, and then the organic solvent is distilled out from the extract under reduced pressure to yield a lipid, primarily composed of triglyceride, containing high concentration of PUFAs. In addition, the resultant lipid, primarily composed of triglyceride, is purified by ordinary processes for edible fats and oils, such as degumming, deoxidation, decolorization, and deodorization to yield high-purity edible fats and oils (triglyceride).

Although the PUFA in a lipid can be directly isolated, it can be readily isolated in the form of ester with a lower alcohol such as methyl ester from the other lipid components, and only a desired PUFA can be readily isolated from the other PUFAs. Such isolation techniques are known in persons skilled in the art.

The microbial cell of the present invention can be utilized as it is or in the form of the dried state. In addition, a PUFA and a lipid containing a PUFA produced by a method of the present invention can also be utilized in various applications. These can be added to, for example, foods and drinks including dietary supplements, nutrition compositions, fodders for animals (in particular, pet foods), aquaculture foods for fish and shellfish, and powdered milk using the techniques known in persons skilled in the art according to the description in, for example, Example below. The preferred intake of PUFAs, in particular, ARA and DGLA is described in, for example, Non-Patent Literature 1.

As mentioned above, the above foods and drinks with high content of PUFA, in particular, DGLA can be readily prepared using the microbial cells according to the present invention even if a low content of microbial cells are used. For example, a pet food containing about at least 100 mg of DGLA in 100 g of pet food can be obtained by adding 0.5 w/w % of dry microbial cells. In addition, triglyceride extracted from the microbial cells mentioned above and purified has very high DGLA content in the total fatty acids, and is suitable for edible fats and oils.

It is permitted that specific applications (for example, nutritious supplement, growth promotion, health promotion, supply of specific fatty acids (for example, DGLA and ARA), and brain function improvement) and/or specific usage (for example, amount, times, and period) are indicated for the (dry) microbial cells mentioned above, a PUFA or a lipid containing a PUFA, or foods and drinks containing one of these.

EXAMPLES

The present invention will be described in detail below by nonlimiting Examples. Note that *Mortierella alpina* 1S-4 produces a lipid containing ARA during Examples. *Mortierella alpina* S14 is a mutant strain induced from *Mortierella alpina* 1S-4 by the inventors, in which the Δ5-desaturase activity for converting DGLA, which is a direct precursor of ARA, into ARA is almost lost. That is, the strain does not substantially produce ARA, but produces a lipid with a high content of DGLA (see Non-Patent Literature 1). *Mortierella alpina* Iz3 also does not substantially produce ARA, but produces a lipid with a high content of DGLA, like S14.

Example 1

Effect of Organic Acid Addition in Test-Tube Culture

Approximately one platinum loop of *Mortierella alpina* S14 was inoculated to 10 mL of liquid culture medium containing soybean powder (3 w/w % glucose, 1.5 w/w % soybean powder, 0.3 w/w % $K_2HPO_4$, 0.1 w/w % $Na_2SO_4$, 0.05 w/w % $MgCl_2 \cdot 6H_2O$, and 0.05 w/w % $CaCl_2 \cdot 2H_2O$, pH 6.3) in a test tube, and was shaking-cultured at 28° C. for three days. In four days after the beginning of the culture, a 50 w/w % sterilized glucose solution was added to 0.6 mL of the culture medium, to which 0.6 mL of aqueous solution of organic acid having a concentration of 5 w/v % after adjustment of the pH to 6.0 with NaOH was also added for further culture (shaking culture). The concentration of the organic acid on the total volume of the culture medium was about 0.3 w/v %. The following organic acids were used; succinic acid, fumaric acid, pyruvic acid, lactic acid, citric acid, tartaric acid, and acetic acid. The control culture medium was prepared by the same procedure except that no organic acid solution was added.

The culture was terminated in ten days after the inoculation, and the resultant dry cell was methyl-esterified by the technique described in JP-A-2000-69987. The resultant fatty acid methyl ester was analyzed by gas chromatography. Specifically, the cultured cell was obtained from the culture solution through filtration after the completion of the culture, and was thoroughly washed and then dried by oven heating (100° C.) to yield a dry cell. The resultant dry cell was placed in a screw-cap test tube (16.5 mm in diameter), to which 1 mL of methylene chloride and 2 mL of anhydrous methanol-hydrochloric acid (10%) were added. The fatty acid residue in the cell was methyl-esterified by treatment at 50° C. for 3 hours, to which were added 4 mL, of n-hexane and 1 mL of water. The mixture was extracted twice, and the solvent in the extract was distilled by a centrifugal evaporator (40° C., one hour) to yield a fatty acid methyl ester. The resultant fatty acid methyl ester was analyzed by capillary gas chromatography for determination of the DGLA content. The results are shown in Table 1.

TABLE 1

| Organic acid (0.3 w/v %) | Dry cell weight (mg/mL of culture medium) | DGLA content per dry cell weight (mg/g of dry cell) | DGLA content per unit volume of culture medium (mg/mL of culture medium) |
| --- | --- | --- | --- |
| None | 32.9 | 164 | 5.39 |
| Succinic acid | 33.7 | 187 | 6.28 |
| Fumaric acid | 33.0 | 182 | 6.01 |
| Pyruvic acid | 33.4 | 179 | 5.97 |
| Lactic acid | 34.8 | 166 | 5.77 |
| Citric acid | 31.6 | 162 | 5.12 |
| Tartaric acid | 28.9 | 139 | 4.03 |
| Acetic acid | 12.1 | 81 | 0.98 |

The dry cell weight per unit volume of the culture medium, the DGLA content per dry cell weight, and the DGLA content per unit volume of the culture medium were increased by addition of succinic acid, fumaric acid, pyruvic acid, and lactic acid, but were not increased by addition of citric acid, tartaric acid, and acetic acid.

Example 2

Effect of Organic Acid Addition in Flask Culture

Approximately one platinum loop of *Mortierella alpina* S14 was inoculated to 100 ml of liquid culture medium containing yeast extract (8 w/w % glucose, 1.5 w/w % yeast extract, 0.3 w/w % $K_2HPO_4$, 0.1 w/w % $Na_2SO_4$, 0.05 w/w % $MgCl_2 \cdot 6H_2O$, and 0.05 w/w % $CaCl_2 \cdot 2H_2O$, pH 6.3) in a flask, and was shaking-cultured at 28° C. for five days. In six days after the beginning of the culture, 2 ml of 10 w/v % lactic acid solution after adjustment of the pH to 6.0 using NaOH was added for further culture (shaking culture). The concentration of the lactic acid based on the total volume of the culture medium was about 0.2 w/v %. The culture was terminated in ten days of the inoculation. A dry cell was obtained as in Example 1, and the DGLA content was measured. The results are shown in Table 2.

TABLE 2

| Lactic acid | Not added | Added |
|---|---|---|
| Dry cell weight (mg/mL of culture medium) | 13.8 | 14.9 |
| DGLA content for dry cell weight (mg/g of dry cell) | 75.3 | 98.4 |
| DGLA content per unit volume of culture medium (mg/mL of culture medium) | 1.04 | 1.47 |
| Percentage of DGLA in total fatty acids (%) | 33.5 | 34.7 |

Addition of lactic acid led to an increase in the dry cell weight per unit volume of the culture medium, the DGLA content per dry cell weight, and the DGLA content per unit volume of the culture medium. Furthermore, the percentage of the DGLA in the total fatty acids contained in the resultant lipid was increased.

Example 3

Effect of Organic Acid Addition in Jar Fermentor Culture

One platinum loop of *Mortierella alpina* S14 was inoculated to 100 mL of seed culture medium (2 w/w % glucose and 1 w/w % yeast extract, pH 6.3), and was precultured for three days with reciprocal shaking of 100 rpm at 28° C. to prepare a seed culture solution. Then, 5 L of main culture medium (2 w/w % glucose, 1.5 w/w % soybean powder, 0.1 w/w % glycerol, 0.2 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3) was fed into a 10 L aeration spinner culture vessel and the mixture was sterilized. After the entire seed culture solution was added to the vessel, aeration spinner culture (main culture) was carried out at 26° C. for seven days at an aeration rate of 1 vvm (air, which was also used in Examples hereafter) and a stirring rate of 300 rpm. Glucose was continuously supplied if required in response to the glucose consumption such that the glucose was always present in the culture medium. In four days after the beginning of the main culture, which was around the time after the logarithmic growth stage and the beginning of the fatty acid accumulation stage, an organic acid solution (succinic acid, fumaric acid, or lactic acid) after adjustment of the pH to 6.3 by NaOH was added such that the final concentration was 0.3 w/v %. Thereafter, the aeration spinner culture was continued. In seven days after the beginning of the main culture, a dry cell was obtained as in Example 1 for determination of the DGLA content. The results are shown in Table 3.

TABLE 3

| | Organic acid (0.3 w/v %) | | | |
|---|---|---|---|---|
| | None | Succinic acid | Fumaric acid | Lactic acid |
| Dry cell weight (mg/mL of culture medium) | 29.6 | 29.4 | 29.6 | 30.5 |
| DGLA content for dry cell weight (mg/g of dry cell) | 199 | 222 | 223 | 203 |
| DGLA content for per unit volume of culture medium (mg/mL of culture medium) | 5.88 | 6.54 | 6.5S | 6.21 |
| Percentage of DGLA in total fatty acids (%) | 37.2 | 40.1 | 38.2 | 37.8 |

Addition of succinic acid, fumaric acid, or lactic acid led to an increase in the DGLA content per dry cell weight and the DGLA content per unit volume of the culture medium. Furthermore, the percentage of the DGLA in the total fatty acids contained in the resultant lipid was increased. In particular, the increase due to addition of succinic acid or fumaric acid was remarkable.

Example 4

Effect of pH Control After Inoculation I

Figure 1B:
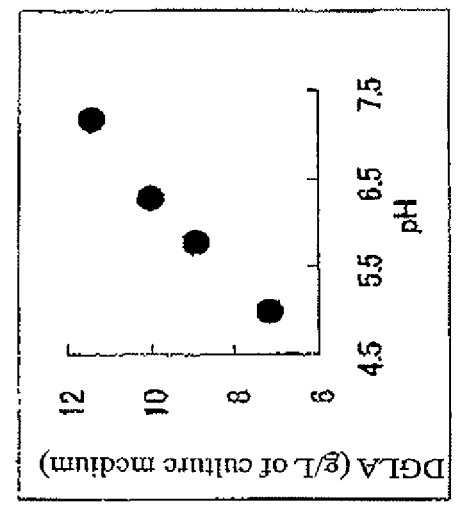
Figure 1C:
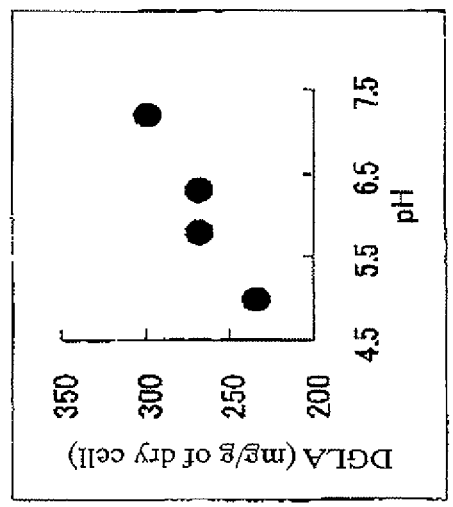

Approximately one platinum loop of *Mortierella alpina* S14 was inoculated to 100 mL of seed culture medium (2% glucose and 1% yeast extract, pH 6.3) and precultured for three days with reciprocal shaking of 100 rpm at 28° C. to prepare a seed culture solution. Then, 5 L of main culture medium (2 w/w % glucose, 1.5 w/w % soybean powder, 0.02 w/w % glycerol, 0.2 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3) was fed into a 10 L aeration spinner culture vessel and the mixture was sterilized. After the entire seed culture solution was added to the vessel, aeration spinner culture (main culture) was carried out at 26° C. for thirteen days at an aeration rate of 1 vvm and a stirring rate of 300 rpm. Glucose was continuously supplied if required in response to the glucose consumption such that the glucose was always present in the culture medium. The pH was adjusted to 5.0, 5.8, or 7.2 with a sterilized NaOH solution or sulfuric acid in five days after the main culture until the end of the culture, which was around the time after the logarithmic growth stage and the beginning of the fatty acid accumulation stage. Note that the pH of the control group without pH adjustment in five days after the beginning of the main culture was about 6.3. In thirteen days after the beginning of the main culture, a dry cell was obtained as in Example 1, and the DGLA content was measured. The results are shown in FIGS. 1A to 1C, wherein the horizontal axis represents the pH value on the fifth day of the culture.

A lower pH (lower than pH 6.3 of the control group) controlled on the fifth day of the culture led to low productivity of DGLA from the microorganism, while a higher pH (higher than pH 6.3 of the control group) led to high productivity of DGLA from the microorganism.

Example 5

Effect of pH Control after Inoculation II

Figure 2A:
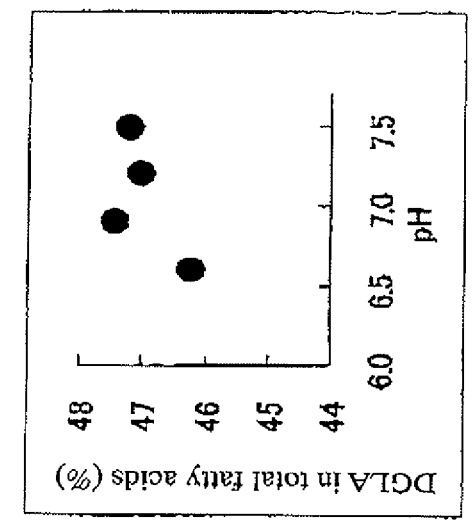
FIGS. 2A to 2C are graphs showing the effects on the DGLA content in cases where the pH was controlled (at pH 6.6, 6.9, 7.2, 75) in three days after the beginning of the main culture of *Mortierella alpina* S14 in Example 5.
Figure 2B:
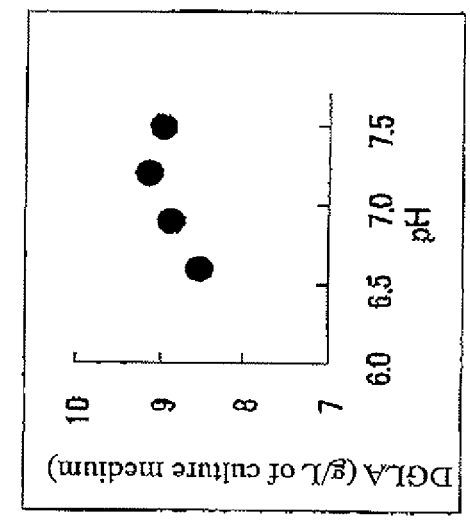
Figure 2C:
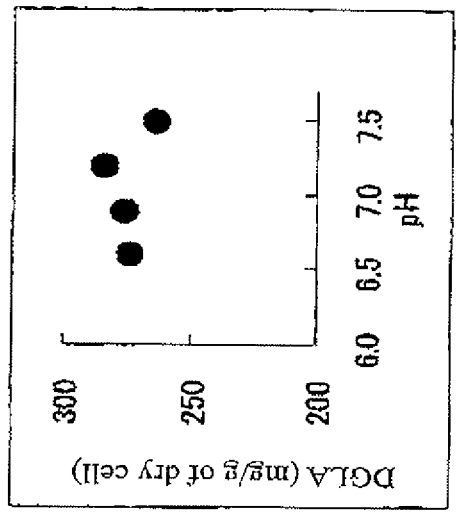

*Mortierella alpina* S14 was cultured as in Example 4 (pre-culture for three days and main culture for eleven days). Glucose was continuously supplied if required in response to the glucose consumption such that the glucose was always present in the culture medium. In three days from the beginning of the main culture to the end of the culture, which was around the time after the logarithmic growth stage and the beginning of the fatty acid accumulation stage, the pH was adjusted to 6.6, 6.9, 7.2, or 7.5 with a sterilized NaOH solution or sulfuric acid. In eleven days after the beginning of the main culture, a dry cell was obtained as in Example 1, and the DGLA content was measured. The results are shown in FIGS. 2A to 2C, wherein the horizontal axis represents the pH value on the third day of the culture.

The pH was controlled on the third day of the culture. The pH adjusted to 6.9 or 7.2 led to an increase in the productivity of DGLA from the microorganism compared with a case of the pH adjusted to 6.6 or 7.5. In addition, the pH control in three and five days after the beginning of the main culture led to an increase in the productivity of DGLA. Thus, the pH was able to be controlled around that time after the beginning of the main culture and convenient for the culture operation.

Example 6

Effect of pH Control after Inoculation III

*Mortierella alpina* 1S-4 was cultured as in Example 4 (preculture for three days and main culture for seven days). Glucose was continuously supplied if required in response to the glucose consumption such that the glucose was always present in the culture medium. In four days after the beginning of the main culture, the pH of the culture medium was adjusted from 6.6 to 6.8 with a sterilized NaOH solution. Thereafter, the pH was not particularly controlled. In seven days after the beginning of the main culture, a dry cell was obtained as in Example 1, and the ARA content was measured. The results are shown in Table 4.

TABLE 4

| pH control | Not controlled | 6.6→6.8 |
|---|---|---|
| Dry cell weight (mg/mL of culture medium) | 40.0 | 34.3 |
| ARA content for dry cell weight (mg/g of dry cell) | 140 | 206 |
| ARA content per unit volume of culture medium (mg/mL of culture medium) | 5.30 | 7.07 |
| Percentage of ARA in total fatty acids (%) | 31.1 | 37.9 |

The pH controlled on the fourth day of the culture led to an increase in the productivity of ARA from the microorganism compared with the case of uncontrolled pH.

Example 7

Method for Adding Organic Acids

*Mortierella alpina* S14 was cultured as in Example 4 (preculture for three days and main culture for ten days). Glucose was continuously supplied if required in response to the glucose consumption such that the glucose was always present in the culture medium. In four days, or in four and seven days after the beginning of the main culture, a sodium salt solution of succinic acid or lactic acid was added such that the final concentrations were those given in Table 5. Note that, the pH values of the culture media of A to D in Table 5 were adjusted to about 6.9 with a NaOH solution on the fourth day of the main culture. In ten days after the beginning of the main culture, a dry cell was obtained as in Example 1, and the DGLA content was measured. The results are shown in Table 5.

TABLE 5

| Organic acid to be added (w/v % culture medium) | | Control | A | B | C | D |
|---|---|---|---|---|---|---|
| Succinic acid | 4th day | 0 | 0.22 | 0.22 | 0.22 | 0.44 |
| | 7th day | 0 | 0 | 0.22 | 0 | 0 |
| Lactic acid | 7th day | 0 | 0 | 0 | 0.22 | 0 |
| Dry cell weight (mg/mL of culture medium) | | 34.6 | 36.8 | 36.6 | 36.9 | 39.1 |
| DGLA content for dry cell weight (mg/g of dry cell) | | 220 | 227 | 243 | 228 | 241 |
| DGLA content for per unit volume of culture medium (mg/mL of culture medium) | | 7.60 | 8.33 | 8.90 | 8.40 | 9.41 |
| Percentage of DGLA in total fatty acids (%) | | 40.9 | 40.8 | 43.0 | 41.2 | 42.2 |

Addition of succinic acid or lactic acid into a final concentration of 0.22 w/v % or 0.44 w/v % on the fourth or seventh day of the main culture had led to an increase in the DGLA content per dry cell weight and the DGLA, content per unit volume of the culture medium. Combined addition of succinic acid and lactic acid was also effective.

Example 8

Amount of Succinic Acid to be Added

Approximately one platinum loop of *Mortierella alpina* S14 was inoculated to 100 ml of seed culture medium (2 w/w % glucose and 1 w/w % yeast extract, pH 6.3) and precultured for three days with reciprocal shaking of 100 rpm at 28° C. to prepare a seed culture solution. Then, 5 L of main culture medium (2 w/w % glucose, 1.5 w/w % soybean powder, 0.02 w/w % glycerol, 0.1 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3) was fed into a 10 L aeration spinner culture vessel and the mixture was sterilized. After the entire seed culture solution was added to the vessel, aeration spinner culture (main culture) was carried out at 26° C. for eleven days at an aeration rate of 1 vvm and a stirring rate of 300 rpm. Glucose was continuously supplied if required in response to the glucose consumption such that the glucose was always present in the culture medium. In four days after the beginning of the main culture, a sodium salt solution of succinic acid was added such that the final concentration was 0.44, 0.87, or 1.3 w/v %. Note that the pH of the culture medium was adjusted to about 6.9 with a NaOH solution in four days after the beginning of the main culture in every case. In eleven days after the beginning of the main culture, a dry cell was obtained as in Example 1, and the DGLA content was measured. The results are shown in Table 6.

TABLE 6

| Succinic acid to be added | 0.44 w/v % | 0.87 w/v % | 1.3 w/v % |
|---|---|---|---|
| Dry cell weight (mg/mL of culture medium) | 37.3 | 37.6 | 37.2 |
| DGLA content for dry cell weight (mg/g of dry cell) | 225 | 228 | 211 |
| DGLA content for per unit volume of culture medium (mg/mL of culture medium) | 8.39 | 8.57 | 7.87 |
| Percentage of DGLA in total fatty acids (%) | 40.0 | 40.4 | 39.2 |

Addition of succinic acid with a concentration of 0.87 w/v % or 1.3 w/v % led to productivity equivalent to that in the case of a concentration of 0.44 w/v %. This elucidates that the DGLA content does not necessarily increase in response to an increase in the amount of the organic acid to be added exceeding a certain level, so that the organic acid can be added in an amount exceeding a certain level.

Example 9

Effect of Mane Acid

*Mortierella alpina* S14 was culture as in Example 8 (pre-culture for three days and main culture for eight days). Glucose was continuously supplied if required in response to the glucose consumption such that the glucose was always present in the culture medium. In four days after the beginning of the main culture, a sodium salt solution of malic acid was added such that the final concentration was 0.71 w/v %. Note that, the pH of the culture medium was adjusted to about 6.9 with a NaOH solution in four days after the beginning of the main culture in every case. In eight days after the beginning of the main culture, a dry cell was obtained as in Example 1, and the DGLA content was measured. The results are shown in Table 7.

TABLE 7

| Malic acid to be added | None | 0.71 w/v % |
|---|---|---|
| Dry cell weight (mg/mL of culture medium) | 34.0 | 36.3 |
| DGLA content for dry cell weight (mg/g of dry cell) | 197 | 207 |
| DGLA content for per unit volume of culture medium (mg/mL of culture medium) | 6.71 | 7.53 |
| Percentage of DGLA in total fatty acids (%) | 39.4 | 38.7 |

Addition of malic acid led to production of microbial cells with high DGLA content.

Example 10

Effect of Succinic Acid in Production of DGLA from Other Strains

Approximately one platinum loop of *Mortierella alpina* Iz3 was inoculated to 100 ml of seed culture medium (2 w/w % glucose and 1 w/w % yeast extract, pH 6.3) and precultured for three days with reciprocal shaking of 100 rpm at 28° C. to prepare a seed culture solution. *Mortierella alpina* Iz3, a DGLA-producible strain, was prepared by nitrosoguanidine treatment (an ordinary mutation operation) of *Mortierella alpina* S-4 that can produce ARA by the same procedure for *Mortierella alpina* S14. Next, 5 L of main culture medium (2 w/w % glucose, 1.5 w/w % soybean powder, 0.02 w/w % glycerol, 0.2 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3) was fed into a 10 L aeration spinner culture vessel and the mixture was sterilized. After the entire seed culture solution was added to the vessel, aeration spinner culture (main culture) was carried out at 26° C. for nine days at an aeration rate of 1 vvm and a stirring rate of 300 rpm. Glucose was continuously supplied if required in response to the glucose consumption such that the glucose was always present in the culture medium. In four days after the beginning of the main culture, a sodium salt solution of succinic acid was added such that the final concentration was 0.44 w/v %. Note that, the pH of the culture medium was adjusted to about 6.9 with a NaOH solution in four days after the beginning of the main culture in every case. In nine days after the beginning of the main culture, a dry cell was obtained as in Example 1, and the DGLA, content was measured. The results are shown in Table 8.

TABLE 8

| Succinic acid to be added | None | 0.44 w/v % |
|---|---|---|
| Dry cell weight (mg/mL of culture medium) | 31.8 | 34.7 |
| DGLA content for dry cell weight (mg/g of dry cell) | 160 | 186 |
| DGLA content for per unit volume of culture medium (mg/mL of culture medium) | 5.08 | 6.46 |
| Percentage of DGLA in total fatty acids (%) | 34.1 | 36.6 |

Addition of succinic acid led to an increase in productivity of DGLA from *Mortierella alpina* Iz3, like *Mortierella alpina* S14.

Comparative Example 1

Culture of DGLA in 10 kL Culture Vessel

*Mortierella alpina* S14 was used. Approximately one platinum loop of the stock microbial strain was inoculated to a culture medium (pH 6.3) composed of 1 w/w % yeast extract and 2 w/w % glucose to initiate preculture with reciprocal shaking of 100 rpm at 28° C. for three days (the first stage). Then, 30 L of culture medium (pH 6.3) composed of 1 w/w % yeast extract, 2 w/w % glucose, and 0.1 w/w % soybean oil was prepared in a 50 L culture vessel, to which a seed culture solution was inoculated (the first stage) to initiate the preculture for two days (the second stage). Then, a seed culture solution was inoculated to the main culture medium (2 w/w % glucose, 3.1 w/w % soybean powder, 0.02 w/w % glycerol, 0.3 w/w % $K_2HPO_4$, 0.1 w/w % $Na_2SO_4$, 0.05 w/w % $MgCl_2.6H_2O$, 0.05 w/w % $CaCl_2.2H_2O$, 0.1 w/w % soybean oil, and 0.01 w/w % Adekanate, pH 6.3) (the second stage), and the resultant culture media was combined with 6000 L in total of the initial culture solution (culture vessel volume: 10 kL) to initiate the culture at 26° C. under an inner pressure of 200 kPa. The culture was carried out for twelve days while glucose was continuously supplied on the first to the fifth day of the culture in response to the glucose consumption such that the glucose was always present in the culture medium. The pH was not controlled. The pH varied between 6.0 and 6.5, decreased once during the logarithmic growth stage, then gradually returned to the original level, and slightly varied during the fatty acid accumulation stage, as a general trend.

After the end of the culture, 7.9 kL of the culture solution was sterilized at 121° C. for 20 minutes. Then, a wet microbial cell was collected using a horizontal filter press having a pneumatic press mechanism, and hot-air-dried at 100° C. to yield dry microbial cells (moisture content: 2%). The weight of the resultant dry microbial cells per unit volume of the culture medium was 47.2 kg/kL, the DGLA content per dry microbial cell weight was 174 g/kg, the DGLA content per unit volume of the culture medium was 8.18 kg/kL, and the percentage of the DGLA in the total fatty acids was 39.1%. In addition, hexane was added to the dry microbial cell for extraction with gentle shaking at room temperature. The resultant hexane solution was filtrated through a filter paper to remove the solid content, and the filtrate was heated to about 30 to 40° C. under reduced pressure to remove hexane, resulting in triglycerides of fatty acids containing DGLA. The percentage of the DGLA in the total fatty acids in the triglycerides was 38.5%.

Example 11

Culture of DGLA in 10 kL Culture Vessel

Culture of *Mortierella alpina* S14 was initiated with 6000 L in total of initial main culture solution as in Comparative Example 1. The culture was continued for twelve days while glucose was continuously supplied on the first to third, and sixth days of the main culture such that the glucose was always present in the culture medium. In the fourth day of the main culture, 1 w/v % disodium succinate hexahydrate solution (60 kg, about 0.44 w/v % succinic acid) and NaOH (1.26 kg) were added to adjust the pH to 6.9. Thereafter, the pH of the culture medium was maintained at 6.9 to 7 until the end of the culture.

After the end of the culture, a dry microbial cell and triglycerides of fatty acids containing DGLA were obtained as in Comparative Example 1. The weight of the resultant dry microbial cell per volume of the culture medium was 51.8 kg/kL, the DGLA content per weight of the dry microbial cell was 240 g/kg, and the DGLA content per unit volume of the culture medium was 12.43 kg/kL. In addition, the percentage of the DGLA in the total fatty acids in the resultant glycerides was 45.8%.

The amounts of the dry microbial cells and the DGLA contents obtained in Comparative Example 1 and Example 11 are shown in Table 9.

TABLE 9

|  | Comparative Example 1 | Example 11 |
|---|---|---|
| Dry cell weight (kg/kL of culture medium) | 47.2 | 51.8 |
| DGLA content for dry cell weight (g/kg of dry cell) | 174 | 240 |
| DGLA content for per unit volume of culture medium (kg/kL of culture medium) | 8.18 | 12.43 |
| Percentage of DGLA in total fatty acids (%) | 38.5 | 45.8 |

Example 12

Effect of Sulfate Salts in Jar Fermentor Culture

Approximately one platinum loop of *Mortierella alpina* S14 was inoculated to 100 ml of seed culture medium (2 w/w % glucose and 1 w/w % yeast extract, pH 6.3) and precultured for three days with reciprocal shaking of 100 rpm at 28° C. Then, 5 L of main culture medium was fed to a 10 L aeration spinner culture vessel and the mixture was sterilized. After the entire seed culture solution was inoculated to the vessel, culture was carried out at 26° C. for eleven days at an aeration rate of 1 vvm and a stirring rate of 300 rpm. The main culture media, respectively, had the following three compositions:

(i) Chloride Salt and Sodium Sulfate (Control):
2 w/w % glucose, 1.5 w/w % soybean powder, 0.02 w/w % glycerol, 0.2 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3

(ii) Sulfate Salt and Sodium Sulfate:
2 w/w % glucose, 1.5 w/w % soybean powder, 0.02 w/w % glycerol, 0.2 w/w % soybean oil, 0.3 w/w % $K_2HPO_4$, 0.1 w/w % $Na_2SO_4$, 0.05 w/w % $MgSO_4.7H_2O$, and 0.05 w/w % $CaSO_4.2H_2O$, pH 6.3

(iii) Sulfate Salt, Free of Sodium Sulfate:
2 w/w % glucose, 1.5 w/w % soybean powder, 0.02 w/w % glycerol, 0.2 w/w % soybean oil, 0.3 w/w % $K_2HPO_4$, 0.05 w/w % $MgSO_4.7H_2O$, and 0.05 w/w % $CaSO_4.2H_2O$, pH 6.3

Glucose was continuously supplied if required in response to the glucose consumption such that the glucose was always present in the culture medium. In four days after the beginning of the main culture, a sodium salt solution of succinic acid was added such that the final concentration was 0.44 w/v %. Note that, the pH of the culture medium was adjusted to about 6.9 with a NaOH solution in four days after the beginning of the main culture in every case. In eleven days after the beginning of the main culture, a dry cell was obtained as in Example 1 for determination of the DGLA content. The results are shown in Table 10.

TABLE 10

|  | Culture media | | |
|---|---|---|---|
|  | (i) Chloride salt (control) | (ii) Sulfate salt and sodium sulfate | (iii) Sulfate salt, free of sodium sulfate |
| Dry cell weight (mg/mL of culture medium) | 36.7 | 37.7 | 37.0 |
| DGLA content for dry cell weight (mg/g of dry cell) | 206 | 232 | 267 |
| DGLA content for per unit volume of culture medium (mg/mL of culture medium) | 7.6 | 8.7 | 9.9 |
| Percentage of DGLA in total fatty acids (%) | 37.5 | 38.2 | 44.0 |

Use of the "sulfate salt and sodium sulfate" culture medium led to an increase in both the DGLA content per weight of the dry microbial cell and the DGLA content per unit volume of the culture medium compared with the control culture medium. The percentage of the DGLA in the total fatty acids contained in the resultant lipid was also increased. Furthermore, it was found that use of the "sulfate salt and sodium sulfate" culture medium led to a further increase in both contents.

Example 13

Amount of Sulfate Salt in Jar Fermentor Culture

*Mortierella alpina* S14 was cultured (preculture for three days and main culture for eleven days) as in Example 12 except that the main culture medium (pH 6.3) contained 2 w/w % glucose, 1.5 w/w % soybean powder, 0.02 w/w % glycerol, 0.2 w/w % soybean oil, 0.3 w/w % $K_2HPO_4$, 0.01 w/w % $MgSO_4.7H_2O$, and 0.01 w/w % $CaSO_4.2H_2O$. In eleven days after the beginning of the main culture, a dry cell was obtained as in Example 1 for determination of the DGLA content. The weight of the resultant dry microbial cell per volume of the culture medium was 33.7 mg/mL, the DGLA content per weight of the dry microbial cell was 209 mg/g, and the DGLA content per unit volume of the culture medium was 7.03 g/L.

Example 14

Effect of Sulfate Salt on Production of Arachidonic Acid

Approximately one platinum loop of *Mortierella alpina* 1S-4 was inoculated to 100 ml of seed culture medium (2 w/w % glucose and 1 w/w % yeast extract, pH 6.3) and precultured for three days with reciprocal shaking of 100 rpm at 28° C. Then, 25 L of main culture medium was fed to a 50 L aeration spinner culture vessel and the mixture was sterilized. After the entire seed culture solution was inoculated to the vessel, culture was carried out at 26° C. for eight days at an aeration rate of 1 vvm and a stirring rate of 300 rpm. The main culture media, respectively, had the following compositions:

(i) Chloride Salt (Control):
2 w/w % glucose, 3.1 w/w % soybean powder, 0.02 w/w % glycerol, 0.1 w/w % soybean oil, 0.3 w/w % $K_2HPO_4$, 0.1 w/w % $Na_2SO_4$, 0.05 w/w % $MgCl_2.6H_2O$, and 0.05 w/w % $CaCl_2.2H_2O$, pH 6.3

(ii) Sulfate Salt:
2 w/w % glucose, 3.1 w/w % soybean powder, 0.02 w/w % glycerol, 0.1 w/w % soybean oil, 0.3 w/w % $K_2HPO_4$, 0.06 w/w % $MgSO_4.7H_2O$, and 0.06 w/w % $CaSO_4.2H_2O$, pH 6.3

Glucose was continuously supplied if required in response to the glucose consumption such that the glucose was always present in the culture medium. In four days after the beginning of the main culture, a sodium salt solution of succinic acid was added such that the final concentration was 0.44 w/v %. Note that, the pH of the culture medium was adjusted to about 6.9 with a NaOH solution in four days after the beginning of the main culture in every case. In eight days after the beginning of the main culture, a dry cell was obtained as in Example 1 for determination of the ARA content. The results are shown in Table 11.

TABLE 11

| | Culture media | |
|---|---|---|
| | (i) Chloride salt (control) | (ii) Sulfate salt |
| Dry cell weight (mg/mL of culture medium) | 36.5 | 39.3 |
| ARA content for dry cell weight (mg/g of dry cell) | 159 | 182 |
| ARA content for per unit volume of culture medium (mg/mL of culture medium) | 5.80 | 7.17 |
| Percentage of ARA in total fatty acids (%) | 47.0 | 45.8 |

Comparative Example 2

Culture of DGLA with Chloride Salt in 10 kL Culture Vessel

Culture of *Mortierella alpina* S14 was initiated with 6000 L in total of initial culture solution as in Comparative Example 1, except that the main culture medium (pH 6.3) used contained 2 w/w % glucose, 4 w/w % soybean powder, 0.02 w/w % glycerol, 0.3 w/w % $K_2HPO_4$, 0.1 w/w % $Na_2SO_4$, 0.05 w/w % $MgCl_2.6H_2O$, 0.05 w/w % $CaCl_2.2H_2O$, 0.1 w/w % soybean oil, and 0.01 w/w % Adekanate. The culture was continued for 10 days while glucose was continuously supplied on the first, second, third, and sixth days of the culture such that the glucose was always present in the culture medium. On the fourth day of the main culture, a 1 w/v % disodium succinate hexahydrate solution (60 kg, about 0.44 w/v % succinic acid) and NaOH (1.26 kg) were added to adjust the pH to 6.9.

After the end of the culture, a dry microbial cell and triglycerides of fatty acids containing DGLA were obtained as in Comparative Example 1. The weight of the resultant dry microbial cell per volume of the culture medium was 57.3 kg/kL, the DGLA content per weight of the dry microbial cell was 168 g/kg, and the DGLA content per unit volume of the culture medium was 9.31 kg/kL. Furthermore, the percentage of the DGLA in the resultant total fatty acids was 41.8%.

Example 15

Culture of DGLA with Sulfate Salt in 10 kL Culture Vessel

*Mortierella alpina* S14 was cultured as in Comparative Example 2 except that the main culture medium (pH 6.3) used contained 2 w/w % glucose, 4 w/w % soybean powder, 0.02 w/w % glycerol, 0.3 w/w % $K_2HPO_4$, 0.06 w/w % $MgSO_4.7H_2O$, 0.06 w/w % $CaSO_4.2H_2O$, 0.1 w/w % soybean oil, and 0.01 w/w % Adekanate.

After the end of the main culture for ten days, a dry microbial cell and triglycerides of fatty acids containing DGLA were obtained as in Comparative Example 1. The weight of the resultant dry microbial cell per volume of the culture medium was 60.5 kg/kL, the DGLA content per weight of the dry microbial cell was 193 g/kg, and the DGLA content per unit volume of the culture medium was 11.70 kg/kL. Furthermore, the percentage of DGLA in the resultant total fatty acids was 42.3%.

The amounts of the resultant dry microbial cells and the resultant DGLA contents in Comparative Example 2 and Example 15 are shown in Table 12.

TABLE 12

| | Comparative Example 2 | Example 15 |
|---|---|---|
| Dry cell weight (kg/kL of culture medium) | 57.3 | 60.5 |
| DGLA content for dry cell weight (g/kg of dry cell) | 168 | 193 |
| DGLA content for per unit volume of culture medium (kg/kL of culture medium) | 9.31 | 11.70 |
| Percentage of DGLA in total fatty acids (%) | 41.8 | 42.3 |

Example 16-1

Pet Food I

The dry microbial cell produced in Example 11 was milled. The milled dry microbial cell in an amount of 0.5% weight was added to a raw material composed of meat meal, chicken extract, corn, rice, soybeans, vegetable fat and oil, and vitamin mixture to produce a pet food. The resultant pet food (100 g) contained about 120 mg of DGLA, which was a level suitable for use.

Example 16-2

Pet Food

A pet food was produced using a dry microbial cell produced in Example 15, as in Example 16-1. The resultant pet food (100 g) contained about 97 mg of DGLA, which was a level suitable for use.

Example 17

Microorganism Food for Fish Juveniles and Larvae Farming

A rotifer and a brine shrimp used as foods for fish juveniles and larvae farming were grown using the milled dry microbial cell produced in Example 16-1. The method for the growth was follows: After 200 ml of seawater was placed in a 300 ml cistern, 100 individuals/1 ml of rotifers and 20 individuals/1 ml of brine shrimps were allowed to be grown under aeration at 23° C. while dry microbial cells were fed in such an amount that would be 1 g/$10^6$ individual rotifers per day and 1 g/$10^5$ individual brine shrimps per day. Both the rotifers and the brine shrimps consumed dry microbial cells to be grown, resulting in foods containing DGLA. Both are suitable for foods for fish juveniles and larvae farming.

Example 18-1

Production of Purified Edible Triglyceride I

The dry microbial cells produced in Example 11 were subjected to extractive purification process, for example, hexane extraction, degumming, deoxidation, decolorization, or deodorization to produce purified edible triglyceride. The percentage of the DGLA in the total fatty acids was 45.4%. In addition, neither hexane nor heavy metals was detected in the triglyceride, which indicated that the triglyceride was suitable for edible fat and oil.

Example 18-2

Production of Purified Edible Triglyceride II

A purified edible triglyceride was produced using the dry microbial cell produced in Example 15 as in Example 18-1. The percentage of the DGLA in the total fatty acids was 42.0%. In addition, neither hexane nor heavy metals was detected in the triglyceride, which indicated that the triglyceride was suitable for edible fat and oil.

Example 19

Preparation of Capsule Containing Fat and Oil Extracted from Dry Microbial Cell

Gelatin (manufactured by Nitta Gelatin Inc.) and glycerol for food additive (manufactured by Kao Corporation) were mixed at a weight ratio of 100:35, and dissolved in water at 50 to 60° C. to prepare a gelatin coating having viscosity of 2000 cp. Then, the purified edible triglyceride produced in Example 18-1 or 18-2 and vitamin E oil (manufactured by Eisai Co., Ltd.) were mixed at a weight ratio of 100:0.05 to prepare a content. Using the coating and the content, encapsulation and drying are carried out by an ordinary operation to produce a soft capsule containing a content of 180 mg/capsule. This soft capsule was suitable for oral administration.

Example 20

Preparation of Beverage Containing Fat and Oil Extracted from Dry Microbial Cell The purified edible triglyceride produced in Example 18-1 and soybeans lecithin (manufactured by Tsuji Oil Mill Co., Ltd.) were mixed at a weight ratio of 9:1 and were uniformly dispersed in water to prepare a liposome dispersion. This liposome dispersion was added in an amount of 1/100 volume to orange juice, carbonated water, coffee, milk, soybean milk, and potage soup to prepare (produce) beverages as foods according to the present invention. All these beverages were suitable for oral intake.

The invention claimed is:

1. A method for producing a high yield of dihomo-y-linolenic acid (DGLA) comprising cultivating *Mortierella alpina* by an aeration-spinner culture process in a culture medium, and the method further comprising at least the following steps: adding at least one organic acid selected from the group consisting of succinic acid, fumaric acid, pyruvic acid, and malic acid, or a mixture thereof to the culture medium in an amount of 0.2 to 5 w/v % at least three days from the beginning of the culture process and increasing the pH of the culture medium to the range of 6.6 to 7.5 at least three days from the beginning of the culture process.

2. The method according to claim 1, further comprising drying the *Mortierella alpina* and then adding either dry cells or the DGLA derived from the cells to food or to drink.

3. The method according to claim 1, wherein addition of the organic acid and pH adjustment are carried out at different time points from an addition of an initial carbon source to the culture medium.

4. The method according to claim 1, further comprising adding a metal sulfate in an amount of 0.01 to 0.5 w/w % to the culture medium.

5. The method according to claim 4, wherein the metal sulfate is added before the beginning of the culture process.

6. The method according to claim 4, wherein the metal sulfate is selected from the group consisting of $MgSO_4$, $CaSO_4$, $K_2SO_4$, $FeSO_4$, and $MnSO_4$, or a mixture thereof.

* * * * *